United States Patent
Jirjis

(10) Patent No.: US 10,039,916 B1
(45) Date of Patent: Aug. 7, 2018

(54) IMPLANTABLE HIGH VOLTAGE ELECTRODE

(71) Applicant: The United States of America as represented by the Secretary of the Air Force, Washington, DC (US)

(72) Inventor: Michael B Jirjis, San Antonio, TX (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 15/271,298

(22) Filed: Sep. 21, 2016

(51) Int. Cl.
*A61N 1/00* (2006.01)
*A61N 1/05* (2006.01)

(52) U.S. Cl.
CPC .................. *A61N 1/0504* (2013.01)

(58) Field of Classification Search
CPC .................................................. A61N 1/0504
See application file for complete search history.

(56) References Cited

U.S. PATENT DOCUMENTS

2004/0064024 A1* 4/2004 Sommer ............... A61N 1/056
600/374
2010/0137712 A1* 6/2010 Krag ............... A61B 17/32053
600/431

OTHER PUBLICATIONS

Ibey, Plasma membrane permeabilization by trains of ultrashort electric pulses, Bioelectrochemistry, 2010, 79 (1) 114-121.
Ibey, Bipolar nanosecond electric pulses are less efficient at electropermeabilization and killing cells than monopolar pulses, Biochemical and Biophysical Research Communications, 2014, 443(2):568-573.

* cited by examiner

*Primary Examiner* — George Manuel
(74) *Attorney, Agent, or Firm* — AFMCLO/JAZ; Jason Sopko

(57) ABSTRACT

An implantable high voltage electrode includes a shaft having a first end and a second end and an ellipsoid tip disposed at the first end. A terminal is disposed at the second end and the terminal in in electrical communication with the ellipsoid tip. At least a first forward facing barb and at least a first aft facing barb disposed on an exterior face of the shaft. The at least first forward facing bard and the at least first aft facing barb are configured to limit movement of the electrode when implanted in biological tissue.

11 Claims, 1 Drawing Sheet

IMPLANTABLE HIGH VOLTAGE ELECTRODE

RIGHTS OF THE GOVERNMENT

The invention described herein may be manufactured and used by or for the Government of the United States for all governmental purposes without the payment of any royalty.

FIELD OF THE INVENTION

The present invention relates generally to high voltage electrodes and, more particularly, to electrodes possessing features to reduce ionization while improving axial positioning thereof.

BACKGROUND OF THE INVENTION

Various types of electrodes, includes subcutaneous and supracutaneous, find use in the medical arts. Some are configured to receive micro-voltage signals from a biological organism, while others are configured to convey electrical signals from an external system to the organism.

Subcutaneous electrodes configured to impart an electrical signals to an organism may be required to operate under varied voltage and current ranges. The vast majority of modern electrodes used in biomedical applications are designed to transfer a low amount of energy. However, as the delivered energy increases, there is a higher probability of ionization and a risk of arcing that results in insufficient electrical delivery into a resistive load or biological tissue. The majority are simply not designed to function optimally under high voltage, high current paramaters.

Furthermore, while some existing electrode technologies include one or more retention features, they are often not sufficient to retard the electrode from propagating both deeper or shallower within the tissue of interest. Even with a retention features, known electrodes may not be configured to place the tip sufficiently deep into the tissue, while simultaneously remaining insulated from the focused electrical discharge at the tip.

More specifically, prior art apparatus and methods for electrical tissue stimulation involved using a needle, an alligator clip, or short barb to deliver the energy to the biological tissue of interest. Prior art technologies limited the scope of applicable use for numerous reasons. First, the typical probe depth was limited to superficial surfaces and would not allow for varied depth implantation. Also, electrodes previously used were often very thin point sources that undesirably increase the rate of charge distributed towards the very tip of the probe, thus increasing the possibility of ionization and arcing at a spatial location. Lastly, prior art technologies did not provide a satisfactory means to stabilize the electrode in place and thereafter prevent it from sliding further into or out of the biological medium.

As a result, there exists a need in the art for a high voltage capable implantable electrode having retention features and geometries suitable for deep tissue implantation.

SUMMARY OF THE INVENTION

The present invention overcomes the foregoing problems and other shortcomings, drawbacks, and challenges of using implantable electrodes that are configured to reduce corona and ionization while possessing features configured to ensure appropriate placement of the electrode in tissue. While the invention will be described in connection with certain embodiments, it will be understood that the invention is not limited to these embodiments. To the contrary, this invention includes all alternatives, modifications, and equivalents as may be included within the spirit and scope of the present invention.

According to one embodiment of the present invention, an implantable high voltage electrode is provided. The electrode includes a shaft having a first end and a second end and an ellipsoid tip disposed at the first end. A terminal is disposed at the second end and the terminal in in electrical communication with the ellipsoid tip. At least a first forward facing barb and at least a first aft facing barb disposed on an exterior face of the shaft. The at least first forward facing bard and the at least first aft facing barb are configured to limit movement of the electrode when implanted in biological tissue.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

Figures 1A, 1B:
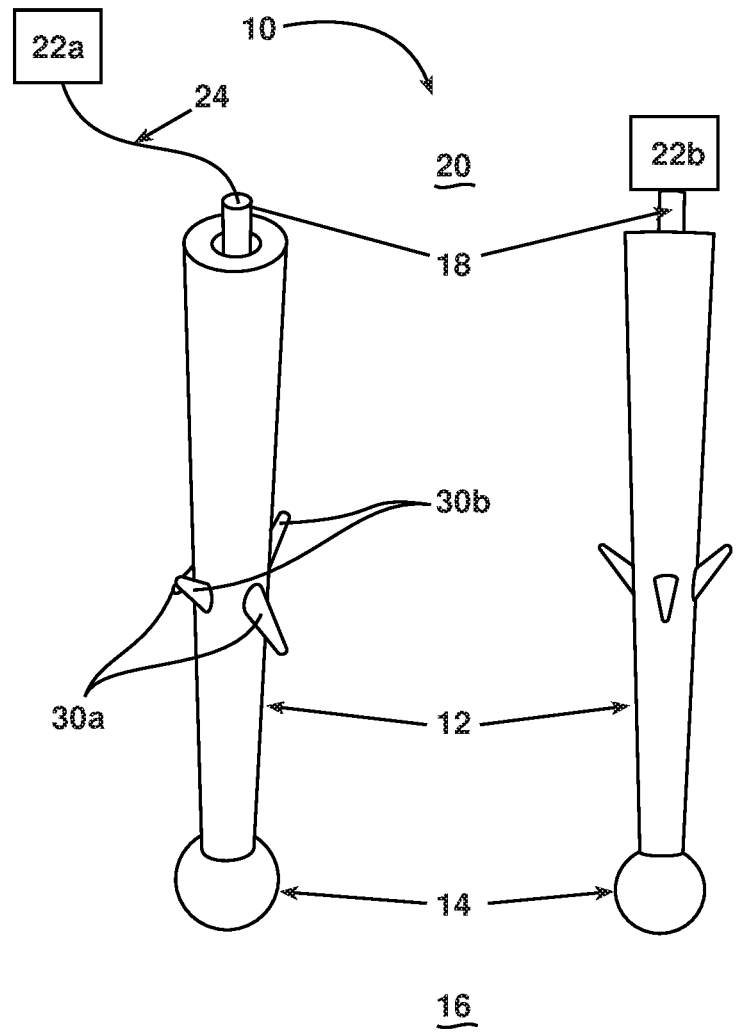
FIGS. 1A and 1B are perspective views according to an embodiment of the disclosed electrode invention.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

Embodiments of the disclosed invention were developed to deliver single or multiple high voltage (1 kV-60 kV) short duration (1 ns-10 μsec) electrical pulses (50-500 Amperes) directly to biological material. Subcutaneous implantation of the electrode increases the probability that the biological material will fully receive the anticipated amount of energy being delivered, and to not lose portions of the energy to other external environmental mediums such as air or water.

This invention has an increased tip surface area that distributes the electrical charge and reduces the chance of ionization while simultaneously allowing for implantation depth into biological material at varying distances from the surface. Once implanted, barbs will securely position and hold the probe in place.

Turning attention to FIGS. 1A and 1B, two perspective views of an embodiment of the disclosed electrode 10 are shown. A shaft 12 include a spherical tip 14 at a forward end 16 and a terminal 18 at an aft end 20. In some embodiments, the shaft 12 is tapered as depicted in FIGS. 1A and 1B, while other embodiments may use a cylinder for the shaft 12 that has a substantially consistent cross sectional area. The spherical tip 14 should be substantially free of burs, points, seams, or other irregularities that may serve to initiate ionization when energized. It should be noted that while the following discussion will continue to describe the spherical tip 14, ellipsoid geometries may be substituted while still producing acceptable results.

The terminal 18 is in electrical communication with the spherical tip 14 and a power supply 22a or 22b may be connected to the terminal 18 and cooperating spherical tip 14. In some embodiments, the shaft 12 is comprised of an electrically insulating material, with the terminal extending from the aft end 20, through the electrically insulating shaft 12, and terminating with the spherical tip 14. In other embodiments, the terminal 18, shaft 12, and spherical tip 14 are fabricated from a monolithic structure or joined from sub-assemblies into a contiguous unit. For example, the electrode 10 may be turned on a lathe, fabricated using additive manufacturing techniques, or assembled so as to establish electrical conductivity between all of the elements 18, 14, and 12. In some embodiments of the disclosed invention, an electrically conductive shaft 12 may be coated with an electrically insulating material. Lacquers, enamels, varnish, urethanes, epoxies, heat shrink tubing, or other coatings may be used with acceptable results.

In some embodiments, the power supply 22a may be connected to the terminals 18 with wires 24 that allow the electrode 10 to be powered from a location remote from a biological tissue in contact with the electrode. In some embodiments, the electrode may be emplaced in biological tissue by launching the electrode 10 as a projectile, with the wires 24 uncoiling to span the distance between the power supply 22a and electrode 10. Other embodiments of the disclosed invention dispose the power supply 22b in direct electrical communication with the terminal 18, such that the power supply 22b is substantially co-located with the electrode 10. Such power supplies 22b may comprise a capacitor or other charge storing, dispensing, and metering components, and the power supply 22b will be propelled with the electrode 10 projectile in such configurations.

The disclosed invention includes one or more barbs 30a and 30b. As shown, barbs 30a are inclined in a forward 16 facing orientation, while barbs 30b are inclined in an aft 20 facing orientation. The barbs 30a and 30b serve to retain the electrode 10 in a given orientation once emplaced into a biological tissue. Once an initial insertion force is overcome and the spherical tip 14 penetrates the tissue to a desired depth, the forward facing barbs 30a limit the electrode 10 from propagating deeper into the tissue, and aft facing barbs 30b serve to limit withdrawal of the electrode 10 from the tissue. The bi-directional barbs 30a and 30b are particularly well suited to retaining the electrode 10 during the violent application of ultra-short duration, high voltage, high current stimulus. For example, unpredictable spastic movements may occur during an application of the high voltage pulse. These movements often cause the electrode's 10 entry wound to open up further, thus causing the probe to penetrate deeper into tissue. In opposition to this undesirable movement of the electrode 10, the bi-directional barbs 30a and 30b help secure the barb into a stable position without the fear of movement during the delivery of the electrical pulse.

Some embodiments of the disclosed invention may use barbs 30a and 30b having an angle of approximately 30 to 45 degrees with respect to the shaft 12, while other embodiments may use an angle of approximately 10 to 15 degrees. Additional embodiments may use asymmetric angles, such that barbs 30a may be disposed at a first angle with respect to the shaft 12, while barbs 30b may be disposed at a second, greater or lesser, angle. For example, forward facing barbs 30a be may be disposed with a shallow angle to reduce the required insertion force, while aft facing barbs 30b may be disposed with a more extreme angle to as to robustly retain the electrode 10 when emplaced in tissue.

In one exemplary embodiment of the disclosed invention, the electrode 10 is approximately 34 mm long, the shaft 12 is tapered and had a 5 mm diameter at its widest point, and a 4 mm diameter spherical tip 14 is provided at the forward end 16. In this configuration, the entire invention is small enough to fit into a #4 gauge needle. Other dimensions and component ratios may be adjusted to achieve design objectives. For example, the sphere can be of varying sizes from 1 mm diameter to 10 mm diameter. Regardless of absolute dimensions, it is desirable to maintain as smooth as a transition between the spherical tip 14 and the shaft 12 as possible so as to avoid initiation points for ionization events. Likewise, the number, placement, and orientation of barbs 30a and 30b may be varied to achieve a balance between considerations of insertion force, withdrawal force, anticipated tissue trauma, and fabrication complexity.

The electrode 10 may be comprised of a bio-suitable conductive metal such as stainless steel, titanium, gold, aluminum, nickel, or alloys, to include stainless steel cobalt chrome, titanium alloy, nickel alloy, and the like. By way of example, the electrode 10 may be fabricated using a direct metal laser melting technology with 40 micron layers of pre-alloyed stainless steel (PH1 type) powder, thereafter post hardened to an approximately 40 Rockwell C Hardness level. After laser fusing or sintering, portions of the electrode may be coated with a class F thermal protection insulating varnish, as discussed above.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. An implantable high voltage electrode, the electrode comprising:
   a shaft having a first end and a second end:
   an ellipsoid tip disposed a the first end, and a terminal disposed at the second end, wherein the terminal is in electrical communication with the ellipsoid tip;
   at least a first forward facing barb and at least a first aft facing barb disposed on an exterior face of the shaft, wherein the at least first forward facing barb and the at least aft facing barb are not retractable with respect to the shaft;

wherein the at least first forward facing barb and the at least first aft facing barb are configured to limit movement of the electrode when implanted in a biological tissue; and wherein the ellipsoid tip is configured to conduct high voltage without ionizing or arcing when implanted in the biological tissue.

2. The electrode of claim 1, wherein the ellipsoid tip is spherical.

3. The electrode of claim 1, wherein the shaft is tapered and has a first cross sectional area proximate the first end, and a second, larger, cross sectional area proximate the second end.

4. The electrode of claim 1, further including a plurality of forward facing barbs and a plurality of aft facing barbs, wherein the forward facing barbs and the aft facing barbs are disposed along an axial ring on the exterior face.

5. The electrode of claim 4, wherein the plurality of forward facing barbs and the plurality of aft facing barbs are disposed at an angle of approximately 15 degrees to approximately 45 degrees with respect to the shaft.

6. The electrode of claim 4 wherein the plurality of forward facing barbs are disposed at a first angle with respect to the shaft and the plurality of aft facing barbs are disposed at a second angle with respect to the shaft.

7. The electrode of claim 6, wherein the first angle is greater than the second angle.

8. The electrode of claim 6, wherein the second angle is greater than the first angle.

9. The electrode of claim 1, further including a plurality of forward facing barbs and a plurality of aft facing barbs, wherein the forward facing barbs and the aft facing barbs are disposed at a plurality of locations on the exterior face between the first end and the second end.

10. The electrode of claim 1, wherein the shaft, forward facing barbs, and aft facing barbs are fabricated from an electrically insulating material.

11. The electrode of claim 1, wherein the shaft, forward facing barbs, and aft facing barbs are coated with an electrically insulating material.

* * * * *